(12) United States Patent
Shell et al.

(10) Patent No.: US 7,674,482 B2
(45) Date of Patent: *Mar. 9, 2010

(54) METHOD AND COMPOSITIONS FOR POTENTIATING PHARMACEUTICALS WITH AMINO ACID BASED MEDICAL FOODS

(75) Inventors: William E. Shell, Los Angeles, CA (US); Elizabeth Charuvastra, Los Angeles, CA (US)

(73) Assignee: Targeted Medical Pharma Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/386,325

(22) Filed: Mar. 22, 2006

(65) Prior Publication Data

US 2006/0159726 A1     Jul. 20, 2006

Related U.S. Application Data

(63) Continuation-in-part of application No. 10/228,765, filed on Aug. 27, 2002, now Pat. No. 7,585,523.

(51) Int. Cl.
| | |
|---|---|
| *A61K 36/00* | (2006.01) |
| *A61K 31/14* | (2006.01) |
| *A61K 31/221* | (2006.01) |
| *A61K 36/16* | (2006.01) |
| *A61K 47/00* | (2006.01) |

(52) U.S. Cl. .................. 424/725; 424/752; 424/439; 514/923

(58) Field of Classification Search .................. None
See application file for complete search history.

(56) References Cited

U.S. PATENT DOCUMENTS

| 3,423,510 | A | * | 1/1969 | Sigg |
| 3,652,769 | A | * | 3/1972 | Saari |
| 4,029,807 | A | * | 6/1977 | Martinez et al. |
| 5,820,867 | A | * | 10/1998 | Bewicke |
| 6,096,317 | A | * | 8/2000 | Desantis et al. |
| 6,153,621 | A | * | 11/2000 | Hamann |
| 6,346,282 | B1 | * | 2/2002 | Cavazza |

* cited by examiner

*Primary Examiner*—Michele Flood
*Assistant Examiner*—Qiuwen Mi
(74) *Attorney, Agent, or Firm*—V Craig Belair; Patton Boggs LLP

(57) ABSTRACT

The methods and compositions for potentiating pharmaceuticals with amino acid based medical foods provides improved cognitive function; induced and maintained sleep; reduced pain, inflammation, blood pressure, anxiety, asthma, duration of viral infection, insulin resistance, and appetite; and treated depression. The amino acid based medical foods, co-packed with at least one selected pharmaceutical, potentiate the pharmaceutical by enhancing the production of neurotransmitters through the oral administration of neurotransmitter precursors, along with natural plant and animal substances that stimulate uptake of the neurotransmitter precursors, cause release of neurotransmitters, cause disinhibition of the neuronal brake, and activate adenylate cyclase in order to avoid tachyphylaxis and prevent pharmacologic tolerance.

2 Claims, 5 Drawing Sheets

METHOD AND COMPOSITIONS FOR POTENTIATING PHARMACEUTICALS WITH AMINO ACID BASED MEDICAL FOODS

CROSS-REFERENCE TO RELATED APPLICATIONS

This application is a continuation in part application of prior U.S. patent application Ser. No. 10/228,765 filed 27 Aug. 2002. The entirety of this application is incorporated herein by reference.

FIELD OF THE INVENTION

This invention relates generally to medical foods that augment neurotransmitter production by simultaneous administration of oral neurotransmitter precursors, a precursor uptake stimulator, a neurotransmitter releaser, a disinhibitor of the adenosine neuron brake, and an activator of adenylate cyclase to prevent tachyphylaxis. The medical foods are combined or co-packed with pharmaceuticals that function through the requisite neurotransmitters. The combined or co-packed medical foods use low dose amino acids to potentiate the drug.

Problem

There has been increasing attention to the role that neurotransmitters and neuromodulators play in various aspects of health and disease. Neurotransmitters are the chemical messengers that allow one neuron to communicate with either a second neuron or an effector organ. Some examples of classic neurotransmitters are acetylcholine and norepinephrine that function within the autonomic nervous system. The autonomic nervous system, operating through its neurotransmitters, controls important body functions, such as heart rate, respiratory rate, gastrointestinal function, appetite, sleep, sexual performance, blood pressure, and mood. Additionally, neurotransmitters and neuromodulators play a crucial role in regulating the function of the cardiovascular, reproductive, musculoskeletal, immune, respiratory, and memory systems.

Numerous pharmaceutical agents have been developed that exert their effects by interfering with one or more of these neurotransmitter or neuromodulator systems. One important pharmaceutical mechanism is that of reuptake inhibition of neurotransmitters in the synaptic cleft of neuron junctions. The pharmaceuticals fluoxetine and fenfluramine are examples of neurotransmitter reuptake inhibitors.

All known neurotransmitters are synthesized within the neurons from their requisite precursor molecules. In addition, administration of neurotransmitter and neuromodulator precursors to subjects has long been known to induce a physiologic response when initially administered. For example, administration of tryptophan—the precursor to the neurotransmitter serotonin—leads to the production of serotonin, administration of choline leads to the production of acetylcholine, administration of tyrosine leads to the production of epinephrine, and administration of arginine leads to the production of nitric oxide. These precursor molecules are generally amino acids and are produced in the liver or are derived from the diet.

Although, the administration of neurotransmitter precursors is known to acutely produce neurotransmitters, as evidenced by a physiologic response, the physiologic response induced by administration of a precursor to a neurotransmitter is often inconsistent, weak in magnitude, and attenuates rapidly such that the precursor administration is largely ineffective. The physiologic loss of neurotransmitter function often results in abnormal physiology and human disease. Moreover, the amount of neurotransmitter precursor that must be administered to elicit a physiologic response is usually several grams, rendering the administration of neurotransmitter precursors impractical.

Some examples of physiologic responses being induced by the administration of a precursor, include U.S. Pat. No. 4,210,637 that describes a composition and method for selectively suppressing the appetite for carbohydrates in a subject by administering tryptophan to produce serotonin concurrently with a carbohydrate to reduce craving for carbohydrates. Later applications of this method included administering tryptophan in subjects in doses up to 2300 mg per day for many days, but did not find consistent appetite suppression because many of the subjects experienced attenuation of the response secondary to tolerance. U.S. Pat. No. 4,309,445 abandoned the use of precursor administration to increase serotonin production and describes a method that focuses on the use of a serotonin reuptake inhibitor, d-fenfluramine, to increase brain levels of serotonin, thereby reducing craving for carbohydrates. The d-fenfluramine and a related molecule, fenfluramine, were subsequently administered to several million humans, a practice discontinued because the reuptake inhibition caused side effects, including heart valve lesions and pulmonary hypertension.

Additionally, U.S. Pat. No. 4,687,763 discloses that tryptophan feeding in conjunction with administration of melatonin can acutely increase brain serotonin concentration and reduce carbohydrate craving; however, it did not examine attenuation or tolerance in this disclosure. U.S. Pat. No. 4,650,789 discloses a method and composition for increasing the production of serotonin by concomitantly administering tryptophan with acetylsalicylic acid; however, it neither disclosed the tolerance or attenuation of the precursor administration nor did it suggest a solution for the attenuation problem. Also, Weintraub observed that phentermine and fenfluramine when used together induced weight loss, reduced appetite and reduced carbohydrate craving in humans; however, weight loss could be obtained for approximately 3 months after which time the effects attenuated and a weight plateau was reached. The patients could only sustain their initial weight loss, but not lose additional weight by maintaining the use of the drugs, or actually increasing the dose of the drugs. The phentermine/fenfluramine combination had induced a physiologic tolerance. If the patients discontinued the drugs, rebound or super-rebound weight gain occurred, frequently returning the patients to their original or greater than original weight.

Also, U.S. Pat. No. 4,673,689 discloses a method for the use of tyrosine to potentiate sympathomimetic agents such as phenylpropanolamine, ephedrine, and pseudoephedrine. The effects described are acute and tolerance is not assessed. The combination of tyrosine with the sympathomimetic agents has not been commercially applied, suggesting that attenuation is an important factor. Such tolerance to sympathomimetic agents is a well-known effect of the use of sympathomimetic agents. Moreover, tolerance is described in the standard texts of pharmacology, where loss of response after successive administration of sympathomimetic agents is experienced. The dose of tyrosine in this disclosure was gram quantities needed to potentiate the sympathomimetic drugs.

U.S. Pat. No. 4,636,494 discloses the administration of choline co-administered with a drug to augment brain production of acetylcholine. It showed inconsistent results with an approximately 50% response rate for a several gram dose of choline. U.S. Pat. No. 6,403,657 discloses the simultaneous administration of a serotonin reuptake inhibitor with a monoamine oxidase inhibitor along with supplementation with 5-hydroxytryptophan and tyrosine to ameliorate the plateau phase of weight loss. U.S. Pat. No. 6,384,008 discloses the use of phentermine and citalopram with both tyrosine and 5-hydroxytryptophan. The doses of the amino acids were large. This reference did not teach the use of low doses of either the amino acids or the drugs.

U.S. Pat. No. 6,436,946 discloses the use of two xanthine-containing components along with neurotransmitter precursors, minerals, nootropic herbs and amino acids to augment the effects of the xanthine components. It discloses several preparations that influence weight loss, effects of stimulants, short-term memory, and hair loss. In each of the formulations presented the observed effects required the ingestion of several grams of xanthine and co-factors for each dose. It did not disclose a solution for the known problem of attenuation of precursor ingestion. It discloses the use of co-factors to augment the effects of xanthine but did not disclose the means for identification of the co-factors or a method for finding the proportion of xanthine and co-factors.

Wurtman has disclosed the co-administration of an amino acid with a pharmaceutical with an amino acid neurotransmitter precursor to potentiate the drug. The dose, however, of the amino acid ranged from 250 mg to many grams per day, and the dose of the pharmaceutical was not reduced. Additionally, U.S. Pat. No. 4,673,689 discloses that tyrosine with a sympathomimetic can prevent tachyphylsaxis of the sympathomimetic. The doses of tyrosine exceeded 140 mg per day and were preferably 700 mg to 7,000 mg per day. Other disclosures include the use of tyrosine in combination with other drugs to avoid undesirable effects, U.S. Pat. No. 4,224,343; potentiate drug effect as antiarrhythmic, U.S. Pat. Nos. 4,271,192 and 4,470,987; prevent tachyphylaxis, U.S. Pat. No. 4,885,312; and increase blood pressure, U.S. Pat. No. 4,327,112. All of these disclosures describe the use of large doses of tyrosine as the amino acid.

Additionally, pharmaceuticals undergo tachyphylaxis and have severe side effects that generally increase with increasing doses. For example, cardiovascular events from rofecoxib (Vioxx®), gastrointestinal effects of aspirin, and sudden death and arrhythmia from cisapride (Propulsid®) are dose related. Valvular heart damage from Fen Phen is dose and time related. When administered alone, pharmaceuticals usually require large and increasing doses. Some classes of pharmaceuticals that require increasing doses include pain drugs, SSRIs, antidepressants, angiolytics, NSAIDs, xanthines, appetite suppressants, sleep agents, antibiotics, antivirals, insulin resistance, antihypertensives, and anti-asthma drugs. At increasing doses, the pharmaceuticals rapidly loose their effectiveness, undergo pharmacologic tolerance, and have increasing side effects that can include death. Also, they have no effectiveness when they are administered in low doses.

Shell has observed in studies dating to 1987 that the initial effects of formulations containing neurotransmitter precursors rapidly attenuate. Appetite suppression from tyrosine acutely occurs but is lost in approximately 7 days. Choline administered in combination with xanthines induces heart rate reduction and altered heart rate variability but the combination attenuated in approximately 7 days. These observations are consistent with the known effects of xanthines, which show attenuation within 7 days of administration. Caffeine attenuation effects are also well known, particularly coffee withdrawal syndrome and altered heart rate. Also, the attenuation of theophylline in the treatment of asthma is well documented, leading to its reduced use in the treatment of asthma.

Therefore, there is a need for an effective means for promoting the production of neurotransmitters and neuromodulators by administration of precursors in acceptable doses, while avoiding the attenuation that frequently occurs with such precursor administration.

Solutions

The above-described problems are solved, and a technical advance is achieved by the present method and compositions for potentiating pharmaceuticals with amino acid based medical foods. The present method and composition for potentiating pharmaceuticals provides compositions that produce results that are both synergistic and surprising. The results indicate that the combination of the five elements of the medical food in combination with a pharmaceutical lead to a result that is more than the individual medical food acting alone. In addition, the effects are sustained and do not attenuate. The effects occurred at concentrations of neurotransmitter precursors significantly less than heretofore achieved. The present method and compositions for potentiating pharmaceuticals includes increasing the production of specific neurotransmitters by not only providing neurotransmitter precursors, but also stimulants to precursor uptake, release of a neuronal inhibiting brake, stimulants to neurotransmilter release, and components to avoid the attenuation previously associated with oral administration of neurotransmitter precursors. The neurotransmitter precursor components are used in combination with a pharmaceutical to reduce the dose of the pharmaceutical and to avoid side effects. The pharmaceutical and precursor combination function by either increasing synthesis of neurotransmitter, altering re-uptake of neurotransmitter, preventing degradation of the neurotransmitter or promoting synergy between the neurotransmitter and the drug.

This invention also provides methods and compositions for formulations of medical foods and dietary supplements that increase the activity of specific neurotransmifters and neuromodulators to use either in combination or co-packing with a pharmaceutical. This invention is based upon the discovery that certain neurotransmitter precursor formulations with synergistic components will act with further synergy with certain pharmaceuticals. This invention describes a method for defining the range of appropriate combinations and concentrations to achieve neurotransmilter production while avoiding tachyphylaxis of amino acids and neurotransmitter dependent pharmaceuticals.

The combinations of neurotransmifter precursors components with low doses of pharmaceuticals provide surprisingly synergistic effects when assessed by specific measurements of physiologic responses. For example, the use of tramadol, a pain drug, with combination with gamma-amino-butyric acid (GABA) and the serotonin precursor 5-HTP reduce intractable pain in the concentrations described in this invention that are less than 25% of the usual dose required to reduce pain. In another aspect of the invention, the precursor formulations provide for the neurotransmitters acetylcholine, epinephrine, norepinephrine, dopamine GABA, glutamate, serotonin, and nitric oxide with the requisite pharmaceutical.

SUMMARY

This invention describes methods and compositions to potentiate pharmaceuticals by enhancing the production of neurotransmitters through the oral administration of neurotransmitter precursors, along with natural plant and animal substances that stimulate uptake of the neurotransmitter precursors, cause release of neurotransmitters, cause disinhibition of the neuronal brake, and activate adenylate cyclase in order to avoid tachyphylaxis and prevent pharmacologic tolerance. The invention describes compositions for medical foods and pharmaceuticals used in combination or by co-packing that are designed to improve cognitive function, induce and maintain sleep, reduce pain, reduce inflammation, improve depression, improve anxiety, reduce blood pressure, reduce asthma, reduce the duration of viral infections, reduce the duration of bacterial infection, reduce insulin resistance, and reduce appetite. The compositions include amino acids such as choline, tyrosine, histidine, arginine, tryptophan, 5-hydroxytrytophan and GABA. The compositions include pharmaceuticals such as tramadol, theophylline, tamazepam, naproxyn, metformin, fluoxetine, trazadone, and amandatine.

DETAILED DESCRIPTION OF THE DRAWINGS

In accordance with the present method and compositions for potentiating pharmaceuticals with amino acid based medical foods ("method and composition for potentiating pharmaceuticals"), it includes enhancing the production of neurotransmitters through the oral administration of neurotransmitter precursors, along with natural plant and animal substances that stimulate uptake of the neurotransmitter precursors, cause release of neurotransmitters, cause disinhibition of the neuronal brake, and activate adenylate cyclase in order to avoid tachyphylaxis and prevent pharmacologic tolerance. The term pharmaceuticals means both prescription and non-prescription drugs. The term medical foods means food products for special dietary use that generally demonstrate greater effectiveness for nutritional management of a specific disease than standard foods and that are intended for subjects with special medically determined nutrient requirements. Medical foods require ongoing medical supervision. Medical foods can be prescribed by physicians.

Figure 1:
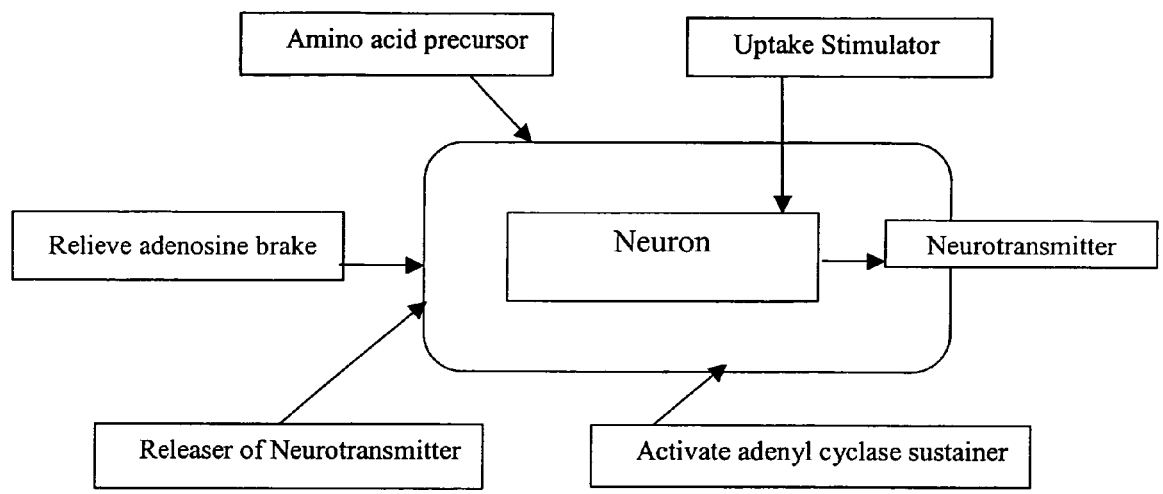
FIG. 1 illustrates an overview of an embodiment of the present method of potentiating pharmaceuticals with amino acid based medical foods.

FIG. 1 illustrates the elements of the composition of the medical food, which can be used in combination with a pharmaceutical of the present method and composition for potentiating pharmaceuticals. These elements include at least one precursor to a neurotransmitter, an uptake stimulator, a component that disinhibits the neuron adenosine brake, a component that promotes the release of a selected neurotransmitter, and a component selected to stimulate adenylate cyclase to avoid attenuation of neurotransmilter production.

The choice of these elements for the compositions of potentiating pharmaceuticals is governed by the neurotransmitter or neuromodulator that interacts with the function of the pharmaceutical (See FIGS. 2-5). It is important that these elements be administered in the correct proportions, and that the precursor is selected correctly. The choice of the precursor determines the neurotransmitter that is synthesized and the subsequent physiologic effect produced. For example, the choice of the precursor choline will lead to the production of the neurotransmitter acetylcholine, which results in a reduced heart rate when the correct elements and proportions are administered (See FIG. 2).

Figure 2:
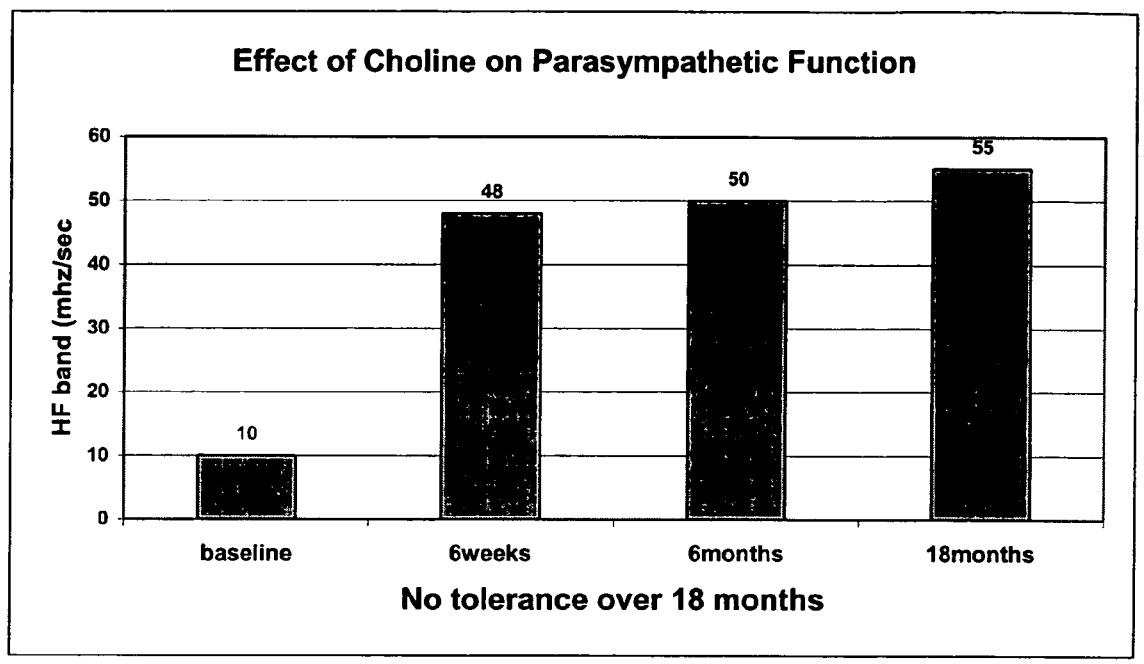
FIG. 2 illustrates a graph of the effects of choline on parasympathetic function of the present method of potentiating pharmaceuticals with amino based medical foods.

FIG. 2 shows the synergistic effects of the formulation of Example 1 (See below) on the parasympathetic autonomic nervous system function of a subject that was measured from 24 hour ambulatory ECG analysis. In this method, the 24 hour period is divided into 254 five minute epochs. The RR-intervals from the ECG recording are subjected to Fast Fourier Transform Analysis for each five minute epoch. In each 5 minute epoch a high frequency band (HF Band) is determined between preferably 0.37 to 0.47 Hz. The area within the HF Band is determined and measured in spectral power ($sec^2$). All 254 HF Bands are then summed to produce a 24 hour total HF Band. The HF Band is a direct measure of parasympathetic function. In FIG. 2, the subject underwent 24 hour ECG monitoring at four times: baseline, 6 weeks, 6 months, and 18 months. Between baseline and 6 weeks parasympathetic function improved and remained stable for 18 months.

In another example, the choice of the precursor tryptophan or 5-hydroxytryptophan results in the production of the neurotransmitter serotonin, which reduces appetite or induces and maintains sleep. Additionally, the choice of the precursor arginine results in the production of the neurotransmitter nitric oxide, which increases vasodilatation and increase in skin temperature (See FIG. 3). The choice of the precursor defines the specificity of the response.

Figure 3:
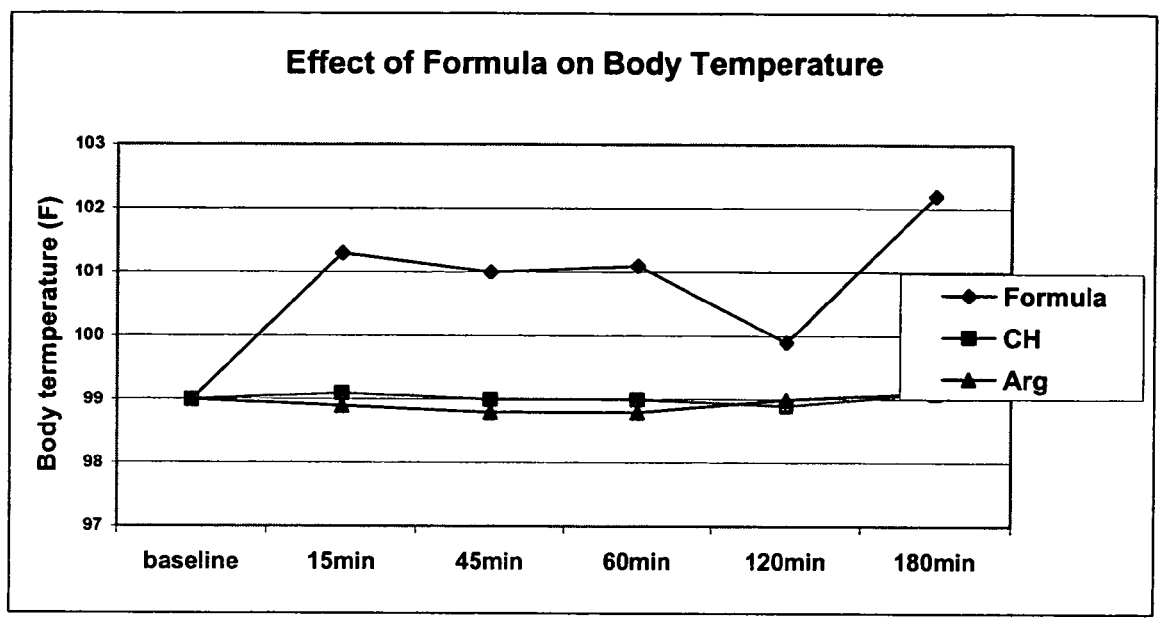
FIG. 3 illustrates a graph of the effects of a formula for increasing the production of nitric oxide on the body temperature of a subject of the present method of potentiating pharmaceuticals with amino based medical foods.

FIG. 3 shows the synergistic effects of the formulation of Example 4 (See below) on the production of nitric oxide by the blood vessels of the skin of a subject that cause vasodilation, which affects an increase in skin temperature. Thus, measurement of the skin temperature of a subject is a convenient assay tool for the production of nitric oxide. In FIG. 3, the formula which contain all five elements of the invention (diamond) increased skin temperature by nearly three degrees over 180 minutes. When only arginine, the nitric oxide precursor, was given alone, no increase in skin temperature was observed. Moreover, when choline as a second control was given, no increase in skin temperature was observed.

Figure 4:
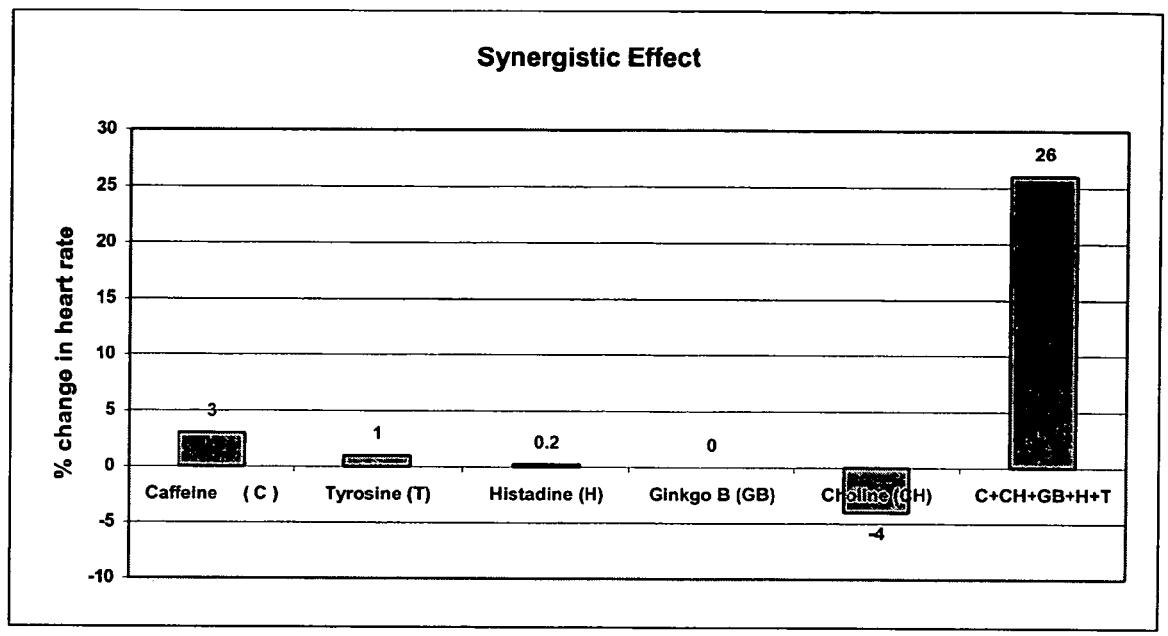
FIG. 4 illustrates a graph of the synergistic effects of the present method of potentiating pharmaceuticals with amino based medical foods.
Figure 5:
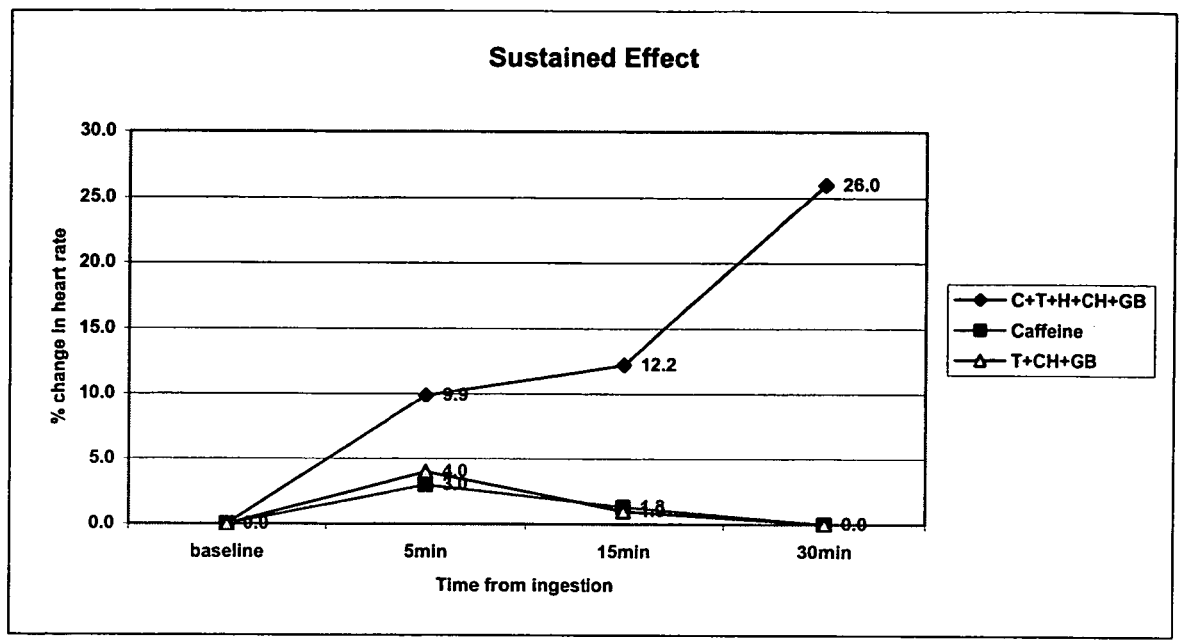
FIG. 5 illustrates a graph of the sustained effects of the present method of potentiating pharmaceuticals with amino based Medical Foods.

More than one precursor can be combined to elicit more than one physiologic response, preferably so long as the precursors do not compete for the same receptor sites (See FIGS. 4 & 5). For example, choline can be combined with 5-hydroxytryptophan to elicit both acetylcholine and serotonin responses. Also, choline and arginine can be combined to elicit both acetylcholine and nitric oxide response. Some exemplary precursors of neurotransmitters that are active in the nervous system and effector organs include choline, glutamic acid, tryptophan, 5-hydroxytryptophan, arginine, and glutamine. The amount of the precursor in the composition for potentiating pharmaceuticals is preferably between 5-300 mg.

FIG. 4 illustrates show the synergistic effects of the formulation of Example 10 on the percent change in heart rate of a subject. In this example heart rate was used to assess the effects of various components of the formula. When all of the components were included, choline, histadine, tyrosine, ginkgo Baloba, and caffeine there was a 26% increase in heart rate 30 minutes after ingestion. When the individual agents were given, there was no change in heart rate. The combination provided a synergistic effect.

FIG. 5 shows the sustained effect on the formulation of Example 10 on the percent change in heart rate of a subject. In this example, change in heart rate was used to assess the effects of various components of the formula of Example 10. In FIG. 5, the "diamond" line represents the formulation of Example 2, which shows a 26 percent change in heart rate after 30 minutes of administering the formulation to a subject. In comparison, the "triangle" line represents a formulation that includes ginkgo biloba, choline, and tyrosine, which shows zero percent change in heart rate after 30 minutes of administering the formulation to a subject. Furthermore, the "square" line represents caffeine, which also shows zero percent change in heart rate after 30 minutes of administering the formulation to a subject. Additionally, caffeine by itself raised the heart rate 4 percent after 5 minutes of administering the caffeine to a subject. Similarly, tyrosine and choline raised the heart rate for 5 minutes when administered together. The combination of the elements raised the heart rate by 26% after 30 minutes of administering the formulation to a subject. The combination did not show attenuation while the individual components rapidly attenuated.

The choice of an uptake stimulator is preferably selected to promote the uptake of the selected precursor. The uptake stimulator can be selected from a drug, herb, or other natural source that stimulates uptake of the precursor of a neurotransmitter. It can be selected from a number of polyphenol containing substances including herbs or other sources including but not limited to ginkgo biloba, which can stimulate the uptake of choline, or cinnamon, which can stimulate the uptake of arginine. Some other exemplary uptake stimulators include glutamine and histadine to promote uptake of the precursor. In addition, pharmaceuticals can also be used as uptake stimulators. The amount of the uptake stimulator in the composition for potentiating pharmaceuticals is preferably between 1-100 mg.

The composition further includes a component that disinhibits the neuron adenosine brake. Preferably, these components are selected from the class of xanthines and sympatheticomimetics. Xanthines are a class of agents that have similar but not identical effects. The xanthines include ephedrine, caffeine, and theobromine, and their potency has generally been ranked according to the ephedrine, caffeine, and theobromine series. The effects of the individual xanthines are not identical. Some exemplary xanthines that can be chosen include theobromine, caffeine, and theophylline. Some exemplary sympatheticomimetics include theophylline, ephedrine, pseudoephedrine, and synephrine. The amount of the component that disinhibites the neuron adenosine brake of the selected neurotransmitter in the composition for potentiating pharmaceuticals is preferably between 1-200 mg.

The composition includes a component that promotes the release of the selected neurotransmitter. The component that stimulates release of neurotransmitters can be selected from a variety of herbs, amino acids, natural sources, and pharmaceuticals. Some exemplary components that stimulate the release of neurotransmitters include ginseng, St. Johns Wort, and glutamate. glutamic acid and glutamine both become glutamate, which is a strong neuroexcitatory amino acid that acts as a neuroexcitatory agent that causes the release of neurotransmitters. Some exemplary amino acids include γ-aminobutyrate, also called 4-aminobutyrate, also known as GABA. In addition, pharmaceutical agents can also be used to release neurotransmilters. The amount of the component that promotes the release of the selected neurotransmitter in the composition for potentiating pharmaceuticals is preferably between 20-100 mg.

The composition for potentiating a pharmaceutical is further enhanced by the addition of a substance that activates adenylate cyclase and prevents the attenuation of neurotransmitter production. The component avoids attenuation by activating adenylate cyclase, and it may be selected from herbs, plant sources, or pharmaceuticals. Some exemplary substances include polyphenol containing herbs, such as hawthorn berry and grape seed extract. Additionally, plant sources may include glycosides, and drugs may include the xanthines: theophylline, caffeine, and ephedrine. The amount of the component that activates adenylate cyclase in the composition for potentiating pharmaceuticals is preferably between 1-200 mg.

The composition for potentiating a pharmaceutical includes a pharmaceutical along with a medical food formulation. Some exemplary pharmaceuticals include tamazepam, lisinopril, amantadine, Valtrex®, mefformin (Glucophage®), modafinil (Provigil®,) piracetam, alprazolam (Xanax®), trazadone, sildenafil citrate (Viagra®,) nitroglycerin, tramadol, rofecoxib (Vioxx®), celecoxib (Celebrex®), morphine, hydrocodone, acetaminophen, oxycodone, codeine, Vicodin®, theophylline, and naproxyn. The amount of the pharmaceutical in the composition for potentiating pharmaceuticals is determined by the individual pharmaceutical used in the composition.

The composition for potentiating pharmaceuticals can be combined into a single capsule or co-packed such that the pharmaceutical and the medical food formulation are in separate capsules. Co-packing of the pharmaceutical and the medical food in separate capsules allows for the titration of both the pharmaceutical and the neurotransmitter precursors provided in the medical food.

In one embodiment, the method and composition for potentitating pharmaceuticals is a combination of the five components that are specifically designed to enhance the function of the parasympathetic component of the autonomic nervous system, which stimulates the synthesis and release of acetylcholine in combination with theophylline or other xanthine drug. The xanthine drug augments neurotransmitter production by relief of the adenosine brake. The combination is designed to improve alertness, cognitive function and energy levels. The components include choline, cocoa, gingko biloba, glutamic acid, and hawthorn berry or grape seed extract. The choline is administered in a range of 20-100 mg. The ginkgo biloba is administered in a range of 50-100 mg. The glutamic acid is administered in a range of 20-100 mg. The hawthorn berry or grape seed extract is administered in a range of 10-40 mg. Cocoa is used as a source of caffeine and theobromine, and is administered in a range of 100-200 mg. the theophylline is given in a range of 1-50 mg.

In another embodiment, the method and composition for potentiating pharmaceuticals is a combination of components designed to augment both serotonin and acetyl choline release. The physiologic endpoint of this embodiment is the induction of sleep and maintenance of deep sleep. The induction of deep delta sleep is activated by brain parasympathetic nervous system activity. The combination of components of this embodiment includes a serotonin precursor, choline or other choline substrate, gingko biloba, cocoa, glutamic acid, and hawthorn berry or grape seed. The serotonin precursor can be either tryptophan or 5-hydroxytryptophan, which are administered respectively, in the range of 10-100 mg. The choline is administered in a range of 20-100 mg., ginkgo biloba in a range of 50-100 mg., glutamic acid in a range of 20-100 mg., and hawthorn berry or grape seed in a range of 10-40 mg. Cocoa is used as a source of caffeine and theobromine and administered in a range of 100-200 mg. If the relative proportions are not maintained, adequate serotonin production does not occur. Without the hawthorn berry or a similar component such as grape seed extract, the induction of sleep activated by precursor administration undergoes rapid attenuation, usually occurring within a couple of days. The pharmaceutical used in this embodiment is tamazepam, and it is given in a dose range of 1-15 mg. The tamazapam acts synergistically with the GABA neurotransmitter. The physiologic effect is measured by assessing the induction of sleep, measurement of sleep stages by polysomnography, and other measurements of sleep quality.

In a further embodiment, the method and composition for potentiating pharmaceuticals is a combination of components designed to augment nitric oxide and acetylcholine production. The physiologic endpoint of this embodiment is an increase in nitric oxide production, increase in heart rate, increase in body temperature, or fall in blood pressure. The combination of components includes arginine, choline, gingko biloba, glutamic acid, and hawthorn berry or grape seed extract. In this embodiment, arginine is administered in the range of 20-100 mg., choline in a range of 20-100 mg., ginkgo biloba in a range of 50-100 mg., glutamic acid in a range of 20-100 mg, and hawthorn berry or grape seed extract in a range of 10-40 mg. Cocoa is used as a source of caffeine and theobromine and is administered in a range of 100-200 mg. This composition includes the pharmaceutical lisinopril and is administered in a dose of 1-20 mg to reduce blood pressure. In this embodiment, the nitric oxide and the lisinopril act synergistically. In addition, a separate composition includes theophylline to reduce asthma. The theophylline is administered in the dose of 1-50 mg. The theophylline acts to increase nitric oxide by relieve of the adenosine brake. In this embodiment the nitric oxide and the theophylline act synergistically.

In yet another embodiment, the method and composition for potentiating pharmaceuticals is a combination of components designed to increase nitric oxide in white blood cells and to simultaneously increase the release of white blood cells in order to fight viral and bacterial infections. The physiologic effect of this embodiment is the increase in white blood cell concentration and a reduction of the symptoms of the viral or bacterial infection. The combination of components includes Echinacea, arginine, choline, cocoa, gingko biloba, glutamic acid, and hawthorn berry or grape seed extract. The Echinacea is administered in the range of 50-100 mg., arginine in the range of 20-100 mg., choline in a range of 20-100 mg., ginkgo biloba in a range of 50-100 mg., glutamic acid is administered in a range of 20-100 mg., and the hawthorn berry or grape seed extract in a range of 10-40 mg. Cocoa is used as a source of caffeine and theobromine and is administered in a range of 100-200 mg. The combined or co-packed pharmaceutical is amantadine or Valtrex® in a dose of 1-100 mg. These pharmaceuticals act synergistically with the nitric oxide.

In a further embodiment, the method and composition for potentiating pharmaceuticals is a combination of components designed to increase norepinephrine, epinephrine, dopamine, histamine, serotonin, and acetylcholine. The physiologic effect of this embodiment is the suppression of appetite, suppression of craving for carbohydrates, fat burning, and increased heart rate. The combination of components includes tyrosine, histidine, tryptophan, choline, gingko biloba, glutamic acid, and hawthorn berry or grape seed extract. The tyrosine is administered in the range of 50-100 mg., Histidine in the range of 20-100 mg., choline in a range of 20-100 mg., ginkgo biloba in a range of 50-150 mg., glutamic acid in a range of 20-100 mg., and hawthorn berry or grape seed extract in a range of 10-40 mg. Cocoa is used as a source of caffeine and theobromine and is administered in a range of 100-200 mg. In order to reduce insulin resistance the combined or co-packed pharmaceutical is Mefformin™, and it is administered in a dose of 1-500 mg. Alternately, in order to potentiate appetite suppression the combined or co-packed pharmaceutical is theophylline, and it is administered in a dose of 1-50 mg. The pharmaceuticals act to increase the synthesis of the neurotransmitters.

The combination of a precursor to a neurotransmitter, an uptake stimulator, a component that disinhibits the neuron adenosine brake, a component that promotes the release of a selected neurotransmitter, a component to stimulate adenylate cyclase to avoid attenuation of neurotransmitter production, and a pharmaceutical may be administered orally or intravenously. Preferably, the combination and proportion is maintained to insure the desired effect. The dosage form may be capsules, suspension caplets, chewable wafers, tablets, or powders.

Acetylcholine deficiencies are involved in diseases such as Alzheimer's disease, diabetes mellitus, chronic fatigue syndrome, fibromyalgia, toxin induced organic brain disease, peripheral neuropathies, autonomic dysregulation, and senile cognitive disorders. These deficiencies are related to memory disorders, muscle fatigue, and peripheral neuropathies. The method and composition for potentiating pharmaceuticals has the advantage of correcting the acetylcholine deficiencies with low dose pharmaceuticals. The pharmaceuticals include theophylline, Provigil®, piracetam and amantadine.

Serotonin deficiencies are involved in diseases such as sleep disorders, anxiety disorders, panic disorders, depression, eating disorders, and chronic pain syndromes. The method and composition for potentiating pharmaceuticals has the advantage of either correcting the serotonin deficiencies or serotonin dysfunction with low dose pharmaceuticals. The pharmaceuticals include alprazolam, trazadone, citalopram, fluoxetine, fluvoxamine, paroxetine and sertraline, Escitalopram, duloxetine, secobarbital (Seconal®) and pentobarbital (Nembutal®), diazepam (Valium®), chlordiazepoxide (Librium®), and chlorazepate (Tranxene®), methaqualone (Quaalude®), ethchlorvynol (Placidyl®), chloral hydrate (Noctec™), and mebrobamate (Miltown®), glutethimide (Doriden®), and methaqualone (Sopor, Quaalude).

Nitric Oxide deficiencies are involved in diseases such as atherosclerosis, hypertension, pulmonary hypertension, sexual dysfunction, immune disorders, infectious disease, peripheral vascular disease, ischemic heart disease, asthma, disorders of bronchoconstriction, and diabetes mellitus. The method and composition for potentiating pharmaceuticals has the advantage of either correcting the nitric oxide deficiencies or dysfunction with low dose pharmaceuticals. The pharmaceuticals include lisinopril, sildenafil citrate (Viagra®), nitroglycerin, chlorthalidone, furosemide, hydrochlorothiazide, metolazone, amiloride hydrochloride, spironolactone, triamterene, acebutolol, atenolol, betaxolol, bisoprolol fumarate, carteolol hydrochloride, metoprolol tartrate, metoprolol succinate, nadolol, propranolol hydrochloride, benazepril hydrochloride, captopril, enalapril maleate, fosinopril sodium, lisinopril, moexipril, quinapril hydrochloride, ramipril, trandolapril, diltiazem hydrochloride, amlodipine besylate, valsartan, losartin potassium, irbesarten, candesartan, amlodipine besylate, felodipine, isradipine, nicardipine, nifedipine, reserpine, hydralazine hydrocholoride, alpha methyldopa, labetolol hydrochloride, carvedilol, prazosin hydrochloride, doxazosin mesylate and terazosin hydrochloride.

Tyrosine deficiencies are involved in disorders of appetite control, mood disorders, and Parkinson's disease. The pharmaceuticals include amandatine, amphetamines, dextroamphetamine (Dexedrine®), phentermine, and methylphenidate.

Glutamate and GABA deficiencies are involved in pain disorders, memory disorders, addictions, anxiety disorders, sleep disorders and depression. The method and composition for potentiating pharmaceuticals has the advantage of correcting either the glutamate deficiencies or dysfunction with low dose pharmaceuticals. The pharmaceuticals include tramadol, rofecoxib, naproxyn celecoxib, morphine, acetophenamin, aspirin, propoxyphene (Darvon®), codeine, hydrocodone (Vicodin®), codeine hydromorphone (Dilaudid®), meperidine Demerol®, diazepam (Valium®), chlordiazepoxide HCl (Librium®), and alprazolam (Xanax®). Some other sedative-hypnotics pharmaceuticals include the benzodiazepines, Diazepam (Valium®), chlordiazepoxide (Librium®), and chlorazepate (Tranxene®), glutethimide (Doriden®), ethchlorvynol (Placidyl®), and methaqualone (Sopor, Quaalude), estazolam (ProSom), gabapentin, zolpidem tartrate, zaleplon, and eszopiclone.

Combinations of neurotransmitter precursors can be used to target more than one neurotransmitter deficiency. For example, the effects of acetylcholine and nitric oxide can be targeted simultaneously. One of the novel aspects of this method and composition for potentiating pharmaceuticals is to simultaneously target two or more neurotransmitter deficiencies using physiologic testing to formulate both the effective combinations and the relative proportions. This combination of multiple neurotransmitters is effective in potentiating pharmaceuticals that can only affect a single neurotransmitter.

The following examples illustrate formulations that produce the desired effect with reduced amounts of pharmaceuticals. All of the following examples derive their effects from the synergistic actions of the individual components.

EXAMPLE 1

Formulation for Production of Acetycholine

In this example, a medical food formulation is prepared to produce acetylcholine and glutamate. It includes combining choline, 600 mg; acetylcarnitine, 100 mg; glutamate, 100 mg; ginkgo biloba, 50 mg; hawthorn berry, 50 mg; cocoa, 400 mg; and dextrose, 200 mg. The total dose is divided into two capsules. A preferred dosage is two capsules in the morning and two capsules at bedtime. The medical food is combined or co-packed with the pharmaceutical theophylline to further inhibit the adenosine brake. The preferred dose of theophylline is 25 mg per day. The medical food co-packed product increases cognitive awareness and perceived energy. For example, a 62-year-old female with fibromyalgia had AM fog and fatigue. Use of the co-packed combination with 25 mg theophylline improved cognitive awareness and abolished AM fatigue. The usual dose of theophylline is 100 mg three or four times per day. The co-packed combination resulted in at least a 75% reduction of theophylline.

EXAMPLE 2

Formulation for Production of Acetycholine and Serotonin

In this example, a medical food formulation is prepared to produce acetylcholine and serotonin for inducing and maintaining sleep. It includes combining choline, 600 mg; acetylcarnitine, 20 mg; 5-hydroxytryptophan, 50 mg; ginkgo biloba, 50 mg; glutamate, 100 mg; cocoa, 400 mg; and dextrose, 200 mg. The total dose is divided into two capsules. A preferred dose to induce and maintain sleep is two capsules at bedtime. The medical food is co-packed with the pharmaceutical tamazepam to reduce sleep latency. The use of the medical food formula alone in a 63-year-old male resulted in a sleep latency of 20 minutes. The co-packed combination of the formula with 7.5 mg of tamazepam resulted in a sleep latency of 10 minutes, a 50% reduction. The usual dose of tamazepam is 30 mg per day. The co-packed combination including 7.5 mg dose of tamazepam resulted in a 75% reduction of tamazepam.

EXAMPLE 3

Formulation for Production of Acetycholine and Serotonin

In this example, a medical food formulation is prepared to produce acetylcholine and serotonin for preventing early awakenings and ameliorate depression. It includes choline, 600 mg; acetylcarnitine, 20 mg; 5-hydroxytryptophan, 50 mg; ginkgo biloba, 50 mg; glutamate, 100 mg; cocoa, 400 mg; and dextrose, 200 mg. The total dose is divided into two capsules. A preferred dose of the medical food to induce and maintain sleep is two capsules at bedtime. The preferred dose to facilitate falling back to sleep after an early reawakening is one capsule. The co-packed combination of the medical food with trazadone, 50 mg at bedtime, resulted in reduced early awakenings and amelioration of depression. In a group of 20 patients with a history of falling asleep but reawakening, the number of reawakening was 4.2 times per night without any treatment, 2.3 times per night on medical food alone, and 0.6 times per night on the co-packed combination. The usual dose of trazadone is 100 mg twice daily. The co-packed combination including 50 mg of trazadone resulted in a 75% reduction of trazadone.

EXAMPLE 4

Formulation for Production of Nitric Oxide and Acetycholine

In this example, a medical food formulation is prepared to produce nitric oxide and acetylcholine for treating asthma and pulmonary hypertension. It includes arginine, 125 mg; choline, 125 mg; glutamine, 25 mg; ginkgo biloba, 50 mg; hawthorn berry, 25 mg; cocoa, 67.5 mg; cinnamon, 50 mg; histidine, 12.5; caffeine, 6.25 mg; and dextrose, 67.5 mg. The total dose is divided into two capsules. A preferred dosage is two capsules, twice daily. The medical food is co-packed with theophylline, 50 mg. The usual dose of theophylline for treatment of asthma is 100 mg several times per day. The co-packed combination including 50 mg of theophylline resulted in at least a 75% reduction of theophylline. Additionally, the high dose of theophylline results in rapid attenuation and major side effects that include agitation and heart irregularities. In an additional example, an 18-year-old female with asthma and reduced FEV1 ingested the formula in example 4;

her FEV1 increased by 50% in 15 minutes. FEV1 is a measure of airflow and is reduced in asthma.

EXAMPLE 5

Formulation for Production of Acetylcholine and Serotonin

In this example, a medical food formulation is prepared to produce a combination of acetylcholine, serotonin, and glutamate for the treatment of fibromyalgia. Fibromyalgia is a condition that involves the autonomic nervous system dysfunction and is related to abnormalities of the midbrain, hypothalamus and amygdale as seen by PET, functional MRI, and spectral MRI. Fibromyalgia is associated with reduced heart rate variability, reduced parasympathetic HF band and failure to activate circadian parasympathetic activity at night. Among the methods to assess autonomic nervous system dysfunction is heart rate variability measured from 24-hour ambulatory electrocardiography, particularly the HF band reflecting parasympathetic autonomic nervous system activity. A 58-year-old female had symptoms of fibromyalgia including point tenderness, sleep disorder AM fatigue and cognitive dysfunction and as autonomic dysfunction; the autonomic dysfunction could be measured as decreased parasympathetic nervous system activity as defined on 24 hour ECG recording of the RR-interval (heart rate variability). In the morning, she took two capsules of the acetylcholine/glutamate preparation described in Example 1 along with theophylline, 50 mg. At bedtime, she took two capsules of the formula described in Example 2 along with trazadone, 50 mg. After six weeks, the sleep disorder had been reduced, AM fatigue was eliminated, and cognitive function improved. Initially, her parasympathetic nervous system function was 20 MHz/sec$^2$ as measured by the high frequency component of the Fast Fourier Transform of the RR-interval frequency distribution (HF-band). Following the 6-week trial of the acetylcholine/glutamate preparation, the parasympathetic function HF-band increased to 48 MHz/sec$^2$, a normal value. Before treatment, her parasympathetic activity failed to increase during night time, but after 6 weeks of treatment it was improved. The improvement continued for 6-months, at which time the HF-band was 50 MHz/sec$^2$. The usual dose of trazadone is 100 mg twice daily and the usual dose of theophylline is 100 mg three times per day for treatment of fibromyalgia.

EXAMPLE 6

Formulation for Production of Nitric Oxide and Acetycholine

A 54-year-old male with hypertension took a preparation designed to increase nitric oxide and acetylcholine. The preparation included ginseng, choline, arginine, hawthorn berry, cocoa, dextrose, and cinnamon. It includes ginseng, 100 mg; arginine, 125 mg; choline, 125 mg; glutamine, 25 mg; ginkgo biloba, 50 mg; hawthorn berry, 25 mg; cocoa, 67.5 mg; cinnamon, 50 mg; histidine, 12.5 mg; caffeine, 6.25 mg; and dextrose, 67.5 mg. The total dose is divided into two capsules. A preferred dosage is two capsules, twice daily. The co-packed combination included lisinopril, 10 mg daily. The baseline blood pressure of this subject was 205/115 mm Hg; the blood pressure was measured daily for 30 days. On the 30th day, the blood pressure of the subject fell to 130/85 mm Hg. The usual dose of lisinopril is 20 to 40 mg daily. The co-packed combination including 10 mg of lisinopril resulted in at least a 50% reduction of lisinopril.

EXAMPLE 7

Formulation for Production of Nitric Oxide, Acetycholine, and White Blood Cell Release A 54-year-old male took a medical food preparation designed to increase nitric oxide, acetylcholine, and white blood cell release in order to ameliorate the effects of oral herpes simplex (cold sore lesions) on the lip. The medical food preparation included choline, arginine, hawthorn berry, cocoa, dextrose, and cinnamon, in combination with 100 mg of Echinacea. It includes Echinacea, 100 mg; arginine, 125 mg; choline, 125 mg; glutamine, 25 mg; ginkgo biloba, 50 mg; hawthorn berry, 25 mg; cocoa, 67.5 mg; cinnamon, 50 mg; histidine, 12.5; caffeine, 6.25 mg; and dextrose, 67.5 mg. The total dose is divided into two capsules. A preferred dosage is two capsules, four times daily. The medical food preparation was co-packed with 100 mg of amandatine daily. The usual dose of amandatine is 100 mg three times per day. At the time of initial symptoms of the oral lesion, he ingested four capsules of the co-packed preparation and repeated the dose every four hours for 48 hours while awake. The lesions disappeared in 24 hours.

EXAMPLE 8

Formulation for Production of Nitric Oxide, Acetycholine, and White Blood Cell Release A 54-year-old male took a medical food preparation designed to increase nitric oxide, acetylcholine, and white blood cell release in order to ameliorate the symptoms of influenza. The medical food preparation included choline, arginine, hawthorn berry, cocoa, dextrose, and cinnamon, in combination with 100 mg of Echinacea. The medical food preparation was co-packed with 100 mg of amandatine daily. At the onset of a sore throat and nasal congestion, he ingested four capsules. The usual dose of amandatine for the treatment of influenza is 100 mg four times daily. In this example the influenza lasted 36 hours. In a comparable group of untreated adults during the same influenza epidemic (n=8), their influenza lasted 7-10 days and required antibiotic therapy to treat secondary infection.

EXAMPLE 9

Formulation for Production of Serotonin and Acetycholine

A 26-year-old Asian male with insomnia for many years duration took the medical food preparation outlined in Example 2 in order to increase serotonin and acetylcholine. The insomnia was characterized as failure to fall asleep for many hours after attempting to initiate sleep, and failure to sleep for more than one hour at a time. He took two capsules each night at bedtime. Within 2 days he began falling asleep within 10 minutes after ingesting the capsules and began to sleep for more than 4 hours. He maintained the improved sleep pattern for three months while taking the preparation each night. When he stopped taking the preparation, his insomnia returned within 3 days. Upon resumption of the preparation, improvement of his sleep pattern returned. In a double blind placebo controlled trial of 18 subjects with insomnia, treated patients reduced there time to fall asleep by 14 minutes from 32 minutes. Placebo treated patients reduced the time to fall asleep by only 4 minutes. The difference between the two groups was significantly different (p<0.001).

in a cohort of these patients, time to fall asleep was reduced to 8 minutes with 7.5 mg tamazepam as a co-pack.

EXAMPLE 10

Formulation for Production of Norephrine, Epinephrine, Dopamine, Histamine, Acetylcholine, and Serotonin In this example, a medical food formulation is prepared to produce a combination of norepinephrine, epinephrine, dopamine, histamine, acetylcholine, and serotonin for suppressing appetite. It includes tyrosine, 50 mg; choline, 600 mg; tryptophan in the form of predigested soy protein, 220 mg; histidine, 100 mg; ginkgo biloba, 120 mg; cocoa, 200 mg; caffeine, 75 mg; and dextrose, 200 mg. A preferred dose is three capsules twice daily. The medical food is co-packed with meffornin, 250 mg or theophylline 50 mg daily to reduce the insulin resistance to amino acid uptake. The usual dose of meffornin is 500 mg four times per day. The usual dose of theophylline is 100 mg four times daily.

EXAMPLE 11

Formulation for Production of GABA, ACTH, Serotonin, Nitric Oxide, and Acetycholine In this example, a medical food formulation is prepared to produce GABA, ACTH, serotonin, nitric oxide and acetylcholine in order to reduce inflammation and acute and chronic pain. It includes GABA, 200 mg; arginine, 75 mg; choline, 125 mg; glutamine, 50 mg; grape seed extract, 25 mg; cocoa, 50 mg; cinnamon, 50 mg; histidine, 50 mg; serine, 25 mg; 5-HTP, 150 mg; and hydrolyzed whey protein, 75 mg. A preferred dosage is two capsules, four times daily. The formula is designed to reduce pain and inflammation.

EXAMPLE 12

Co-Packed Formulation of Naproxyn

In this example, a medical food formula of Example 11 is co-packed with naproxyn for the treatment of arthritis, headache, myalgia, tooth pain, and post-surgical pain. The preferred dosage is two to four capsules daily. The usual dose of naproxyn is 250 mg four times daily. A 42-year-old female was treated for point tenderness associated with fibromyalgia. Pain was abolished for more than four hours per dose without cognitive dysfunction. In a group of 40 patients with mild back and muscle pain, 32 experienced a reduction of pain within 30 minutes of ingestion of the formula.

EXAMPLE 13

Co-Packed Formulation of Tramadol

In this example, a medical food formula of Example 11 is co-packed with tramadol and taken two to four times daily for the treatment of intractable chronic pain that is unresponsive to either Vicodin® or morphine. The dose of tramadol is 250 mg daily. The usual dose of tramaldol is 250 mg four times daily, with poor control of intractable pain. Six patients with intractable pain from cancer (2), arthritis (1), and fibromyalgia (3) were treated with the co-packed combination. Five of the six patients had control of the pain for more than 6 hours after each dose.

Example 14

Co-Packed Formulation of Carisoprodol

In this example, a medical food formula of Example 11 is co-packed with carisoprodol for the treatment of arthritis, headache, myalgia, tooth pain, and post-surgical pain in association strains, sprains, and other muscle injuries. The preferred dosage of example 11 is two to four capsules daily. The usual dose of carisoprodol is 350 mg one to four times daily. A 42-year-old female was treated for point tenderness associated with fibromyalgia. Pain was abolished for more than four hours per dose without cognitive dysfunction.

EXAMPLE 15

Co-Packed Formulation

Formulation for Production of Norephrine, Epinephrine, Dopamine, Histamine, Acetylcholine, and Serotonin In this example, a medical food formulation is prepared to produce a combination of norepinephrine, epinephrine, dopamine, histamine, acetylcholine, and serotonin for suppressing appetite. It includes tyrosine, 50 mg; choline, 600 mg; tryptophan in the form of predigested soy protein, 220 mg; histidine, 100 mg; ginkgo biloba, 120 mg; cocoa, 200 mg; and dextrose, 200 mg. The formula is without caffeine. A preferred dose is three capsules twice daily. The medical food is co-packed with meffornin, 250 mg or theophylline 50 mg daily to reduce the insulin resistance to amino acid uptake. The usual dose of meffornin is 500 mg four times per day. The usual dose of theophylline is 100 mg four times daily.

Although there has been described what is at present considered to be the preferred embodiments of the method and composition for potentiating pharmaceuticals, it will be understood that the compositions can be embodied in other specific forms without departing from the spirit or essential characteristics thereof. For example, lower or higher amounts of the pharmaceuticals or medical foods can be used in addition to the those described herein. The present embodiments are, therefore, to be considered in all aspects as illustrative and not restrictive. The scope of the invention is indicated by the appended claims rather than the foregoing description.

What is claimed:

1. A co-packed medical food combination for producing acetylcholine and serotonin for reducing sleep latency, preventing early awakenings and ameliorating depression comprising a first and a second composition:

a first composition comprising:
from about 20% to about 65%, based on the total weight of said first composition, of choline;
from about 0.7% to about 2.1%, based on the total weight of said first composition, of acetylcarnitine;
from about 1.8% to about 5.3%, based on the total weight of said first composition, of 5-hydroxytryptophan;
from about 1.8% to about 5.3%, based on the total weight of said first composition, of ginkgo biloba;
from about 3.5% to about 10.5%, based on the total weight of said first composition, of glutamate;
from about 14% to about 42%, based on the total weight of said first composition, of cocoa;
from about 7% to about 21%, based on the total weight of said first composition, of dextrose; and a second composition comprising:
   from about 25 mg to about 75 mg of trazadone, wherein said first composition potentiates said second composition for said reducing sleep latency, preventing early awakenings and ameliorating depression.

2. A co-packed medical food combination for producing acetylcholine and serotonin for preventing early awakenings and to ameliorate depression comprising a first and a second composition:
   a first composition comprising:
      from about 20% to about 65%, based on the total weight of said first composition, of choline;
      from about 0.7% to about 2.5%, based on the total weight of said first composition, of acetylcarnitine;
      from about 1.7% to about 5.5%, based on the total weight of said first composition, of 5-hydroxytryptophan;
      from about 1.7% to about 5.5%, based on the total weight of said first composition, of ginkgo biloba;
      from about 3% to about 15%, based on the total weight of said first composition, of glutamate;
      from about 14% to about 45%, based on the total weight of said first composition, of cocoa;
      from about 7% to about 25%, based on the total weight of said first composition, of dextrose; and
   a second composition comprising:
      from about 25 mg to about 75 mg of trazadone, wherein said first composition potentiates said second composition for said preventing early awakenings and to ameliorate depression.

* * * * *